(12) United States Patent
Iijima

(10) Patent No.: US 10,271,813 B2
(45) Date of Patent: Apr. 30, 2019

(54) RADIOGRAPHY SYSTEM, CONTROL METHOD, AND STORAGE MEDIUM

(71) Applicant: CANON KABUSHIKI KAISHA, Tokyo (JP)

(72) Inventor: Tadahiko Iijima, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 335 days.

(21) Appl. No.: 15/076,110

(22) Filed: Mar. 21, 2016

(65) Prior Publication Data

US 2016/0278729 A1 Sep. 29, 2016

(30) Foreign Application Priority Data

Mar. 27, 2015 (JP) ................................. 2015-067070

(51) Int. Cl.
*A61B 6/00* (2006.01)
(52) U.S. Cl.
CPC .............. *A61B 6/54* (2013.01); *A61B 6/4208* (2013.01); *A61B 6/4283* (2013.01); *A61B 6/461* (2013.01); *A61B 6/5205* (2013.01); *A61B 6/5241* (2013.01); *A61B 6/56* (2013.01); *A61B 6/4233* (2013.01)
(58) Field of Classification Search
None
See application file for complete search history.

(56) References Cited

U.S. PATENT DOCUMENTS

| 2006/0054829 | A1 |   | 3/2006  | Tsuchino et al. |
|---|---|---|---|---|
| 2011/0057111 | A1 |   | 3/2011  | Nishino |
| 2011/0286582 | A1 |   | 11/2011 | Iwashita et al. |
| 2012/0049080 | A1 |   | 3/2012  | Enomoto |
| 2016/0074001 | A1 | * | 3/2016  | Matsushita ............ A61B 6/566 378/62 |

FOREIGN PATENT DOCUMENTS

| CN | 102204826 A  | 10/2011 |
|---|---|---|
| CN | 102370489 A  | 3/2012  |
| CN | 103096798 A  | 5/2013  |
| JP | 2002-200064 A | 7/2002  |
| JP | 2012-045159 A | 3/2012  |

* cited by examiner

*Primary Examiner* — Hoon K Song
(74) *Attorney, Agent, or Firm* — Canon USA Inc., IP Division

(57) ABSTRACT

A radiography system for executing long-length imaging by using a plurality of radiation imaging apparatuses includes an acquisition unit configured to acquire respective states of the plurality of radiation imaging apparatuses, and a state control unit configured to shift power consumption of one radiation imaging apparatus to a same state as that of another radiation imaging apparatus based on the respective states acquired by the acquisition unit in a case where at least the one radiation imaging apparatus from among the plurality of radiation imaging apparatuses is in a state where the power consumption is higher than that of the another radiation imaging apparatus.

10 Claims, 7 Drawing Sheets

FIG. 3

| | POWER-OFF STATE | ERROR STATE | STAND-BY STATE | IMAGING PREPARATION COMPLETION STATE | IMAGING EXECUTABLE STATE | IMAGING STATE |
|---|---|---|---|---|---|---|
| RE-IMAGING POSSIBILITY | HIGH | HIGH | HIGH | MIDDLE | LOW | HIGH |
| POWER-SAVING PERFORMANCE | HIGH | HIGH | MIDDLE | LOW | LOW | LOW |
| DURABILITY | HIGH | MIDDLE | MIDDLE | LOW | LOW | LOW |
| PRIORITY | 1 | 2 | 3 | 5 | 6 | 4 |

RADIOGRAPHY SYSTEM, CONTROL METHOD, AND STORAGE MEDIUM

BACKGROUND OF THE INVENTION

Field of the Invention

The present invention relates to a radiography system using a plurality of radiation imaging apparatuses, a control method, and a storage medium.

Description of the Related Art

In recent years, in the medical field, for example, there has been an increasing demand for imaging an observation area having a long length (hereinafter, referred to as "long-length imaging"), such as imaging an entire portion of a spinal cord, a lower extremity, or a body in order to grasp distortion or abnormality in an subject's body. When long-length imaging is executed, for example, radiation may be emitted for a plurality of times with an observation area divided into a plurality of sections, or radiation may be emitted to the entire observation area once. In a case where long-length imaging is executed by a radiography system using a plurality of radiation imaging apparatuses, the imaging is executed while all of the plurality of radiation imaging apparatuses is in an imaging executable state.

Japanese Patent Application Laid-Open No. 2012-45159 discusses a radiography system in which a plurality of radiation imaging apparatuses is arranged in a row.

However, according to the radiography system described in Japanese Patent Application Laid-Open No. 2012-45159, a plurality of radiation imaging apparatuses can be in different states. Therefore, radiation can be emitted even if a part of the plurality of radiation imaging apparatuses is in a state where imaging is not executable (hereinafter, referred to as "imaging non-executable state"). In such a case, the radiography system cannot acquire a part of the image of a region to be captured. Further, in a case where only a part of the radiation imaging apparatuses from among the plurality of radiation imaging apparatuses is turned on, even if the rest the radiation imaging apparatuses are in the imaging non-executable state, there is a risk in which the radiography system may consume unnecessary electricity as the radiography system because there is a radiation imaging apparatus with which imaging is executable.

SUMMARY OF THE INVENTION

The present invention is directed to radiography system for executing long-length imaging, capable of improving the usability even in a case where a plurality of radiation imaging apparatuses included in the radiography system can take different states.

According to an aspect of the present invention, a radiography system for executing long-length imaging by using a plurality of radiation imaging apparatuses includes an acquisition unit configured to acquire respective states of the plurality of radiation imaging apparatuses, and a state control unit configured to shift power consumption of at least one radiation imaging apparatus to a same state as that of another radiation imaging apparatus based on the respective states acquired by the acquisition unit in a case where the at least one radiation imaging apparatus from among the plurality of radiation imaging apparatuses is in a state where the power consumption is higher than that of the another radiation imaging apparatus.

Further features of the present invention will become apparent from the following description of exemplary embodiments with reference to the attached drawings.

BRIEF DESCRIPTION OF THE DRAWINGS

FIG. 3 is a table illustrating a relationship between a radiography system and priority according to the first exemplary embodiment.

DESCRIPTION OF THE EMBODIMENTS

A first exemplary embodiment of the present invention will be described specifically with reference to the appended drawings. Details of a size and a structure described in each exemplary embodiment are not limited to those described in the specification or the drawings. Further, in the specification, the radiation includes an alpha ray, a beta ray, a gamma ray, a particle ray, and a cosmic ray in addition to an X-ray.

Figure 1:
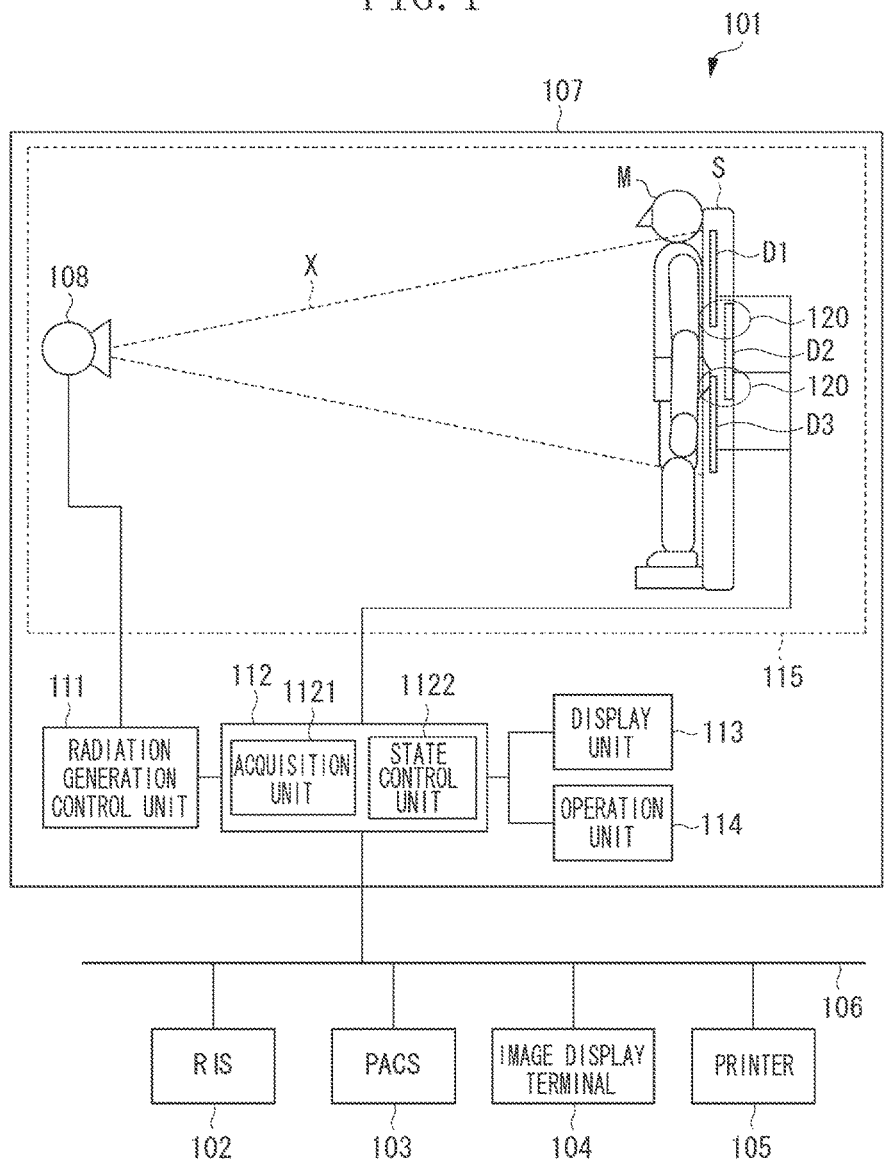
FIG. 1 is a block diagram illustrating a radiography system according to a first exemplary embodiment.

First, a radiography system will be described with reference to FIG. 1. FIG. 1 is a block diagram schematically illustrating a medical diagnosis system.

A medical diagnosis system 101 includes a radiology information system (RIS) 102, a picture archiving and communication systems (PACS) 103, an image display terminal 104, a printer 105, and a radiography system 107. These apparatuses are connected to each other via a communication means 106 such as a network.

The RIS 102 manages operations ranging from reservation of examination or treatment to acquisition of an examination result executed by a radiological device. For example, the RIS 102 may be an information management system that generally manages additional information added to a radiation image or an examination order. The additional information may include examination information such as an examination identification (ID) or a reception number. An operator can input an examination order (examination instruction) through the RIS 102. The radiography system 107 executes imaging according to the examination order. In the present exemplary embodiment, the input examination order is stored and managed by the RIS 102. However, the input examination order may be stored and managed by a server (not illustrated) connected to the RIS 102 and the radiography system 107. As another example, the input examination order may be stored and managed by the radiography system 107.

The PACS 103 saves and manages a radiation digital image (hereinafter, referred to as "captured image") captured by the radiography system 107. In other words, the PACS 103 functions as a part of an image management system that manages a captured image.

The image display terminal 104 can display a captured image saved in the PACS 103 as an output. The printer 105 can print a captured image saved in the PACS 103 as an output.

The radiography system 107 executes examination (i.e., imaging) based on the examination order including a plurality of pieces or examination information. The examination information includes imaging protocol information, and each imaging protocol specifies an imaging condition or content of image processing to be executed on the captured image. More specifically, the imaging protocol includes parameter information or imaging execution information used at an imaging time or an image processing time, and imaging environment information such as a sensor type or an imaging orientation. Further, the examination information includes information such as an examination ID or a reception number that identifies the examination order or information that identifies a captured image according to the examination order.

The radiography system 107 includes a radiation imaging system S and an imaging control unit 112. The radiography system 107 further includes a radiation source 108, a radiation generation control unit 111, a display unit 113, and an operation unit 114. Herein, the radiation imaging system S includes radiation imaging apparatuses D1, D2, and D3. The radiography system 107 can operate in a synchronous imaging mode and an asynchronous imaging mode when imaging is executed. In the synchronous imaging mode, the imaging timing is adjusted to synchronize between the radiation imaging apparatuses D1 to D3, and the radiation source 108. In the asynchronous imaging mode, the radiation imaging apparatuses D1 to D3 respectively start imaging by detecting the incident radiation without synchronizing the imaging timing thereof with the emission timing of radiation.

The radiation source 108 functions as a radiation generation unit. In other words, in the present exemplary embodiment, an X-ray tube serves as the radiation source 108 and emits radiation (X-ray) onto a subject M (i.e., examinee).

Each of the radiation imaging apparatuses D1, D2, and D3 includes a radiation detection panel on which a plurality of pixels is arranged in a two-dimensional matrix state. Each of the pixels includes a sensor and a. switching element in order to convert radiation into an electric signal. The radiation detection panel has a function for converting the received radiation into an image signal, and executes imaging based on the radiation passing through the subject. A direct-conversion sensor such as a sensor configured of an amorphous selenium (a-Se) material, which directly converts radiation into an electric signal, or an indirect sensor that uses a scintillator such as cesium iodide (CsI) and a photoelectric conversion element may he used as the sensor. Further, each of the radiation imaging apparatuses D1, D2, and D3 executes analog-digital (A/D) conversion of the converted electric signal to generate a captured image as radiation image data, and transfers the captured image to the imaging control unit 112.

Each of the radiation imaging apparatuses D1 and D3 is arranged in such a manner that a portion thereof spatially overlaps with a portion of the radiation imaging apparatus D2 when viewed from a radiation source 108 side. Herein, "spatially overlap" may refer to a state where the radiation imaging apparatus D1 (D3) physically contacts and overlaps with the radiation imaging apparatus D2, or may refer to a state where the radiation imaging apparatus D1 (D3) spatially overlaps with the radiation imaging apparatus D2 with no physical contact. Further, the above-described arrangement of the radiation imaging apparatuses D1, D2, and D3 is merely an example, and thus the radiation imaging apparatuses D1, D2, and D3 do not have to spatially overlap with each other. The radiation imaging system S connects the images captured by the radiation imaging apparatuses D1, D2, and D3 to each other to generate one large image in order to acquire a long-length image.

According to the control of the imaging control unit 112, the radiation generation control unit 111 controls generation of radiation based on the imaging protocol. Specifically, according to an imaging condition corresponding to the imaging protocol, e.g., parameters such as a tube current, a tube voltage, and an irradiation time, the radiation generation control unit 111 applies a voltage to the radiation source 108 to generate radiation.

The imaging control unit 112 integrally controls radiation imaging processing based on the imaging protocol.

Further, the imaging control unit 112 executes image processing on the captured image acquired from the radiation imaging system S. The image processing includes combining processing, correction processing, gradation processing, and frequency processing of a plurality of captured images captured by the radiation imaging apparatuses D1, D2, and D3. The imaging control unit 112 executes the image processing by using an image processing parameter according to the imaging protocol. Further, the imaging control unit 112 can transmit the acquired captured images to the external apparatuses such as the PACS 103 and the printer 105. The PACS 103 receives and stores the transmitted captured images together with the examination information for identifying the captured images. For example, the examination information may be an examination ID or a reception number added to the examination order. The PACS 103 may store the captured images in association with the examination order. Further, the imaging control unit 112 can set priority described below. In such a case, the imaging control unit 112 also functions as a setting unit. The imaging control unit 112 further includes an acquisition unit 1121 and a state control unit 1122.

The acquisition unit 1121 acquires respective states (state information) of the plurality of radiation imaging apparatuses D1, D2, and D3. Herein, for example, the states may include a state indicating whether the respective radiation imaging apparatuses D1 to D3 can execute imaging and state indicating whether the radiation imaging apparatuses D1 to D3 are turned on.

In a case where a state of one radiation imaging apparatus from among the plurality of radiation imaging apparatuses D1, D2, and D3 is different from states of other radiation imaging apparatuses, the state control unit 1122 shifts the state of the one radiation imaging apparatus to the same state as that of the other radiation imaging apparatuses based on the states acquired by the acquisition unit 1121.

The display unit 113 displays information such as a state of the radiography system 107 for the operator. In other words, the display unit 113 functions as a display unit for displaying the states of the plurality of radiation imaging apparatuses D1 to D3. In addition, the display unit 113 may display a state of only a part of radiation imaging apparatuses from among the plurality of radiation imaging apparatuses D1 to D3. For example, a display monitor may serve as the display unit 113. For example, the display unit 113 can display an examination order received from the RIS 102 or an examination order created by the operator of the radiography system 107. The operation unit 114 acquires an instruction from the operator. For example, a graphical user interface (GUT) such as a keyboard, a mouse, or a touch-panel, or various buttons may serve as the operation unit 114. For example, the operator can input an instruction for copying an image to the radiography system 107 via the operation unit 114.

Figure 2:
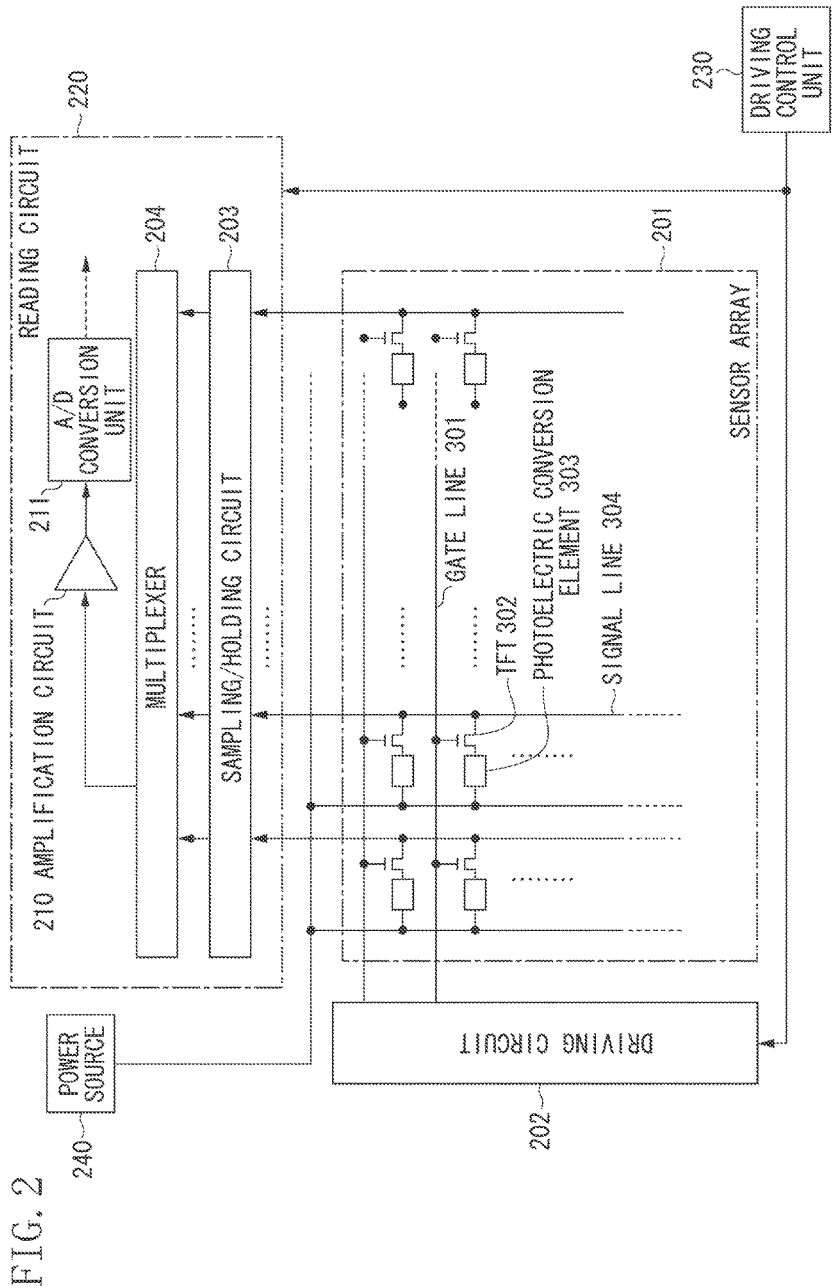
FIG. 2 is a block diagram illustrating radiation imaging apparatus according to the first exemplary embodiment.

Next, a configuration of one of the plurality of radiation imaging apparatuses D1 to D3 according to the present exemplary embodiment will be described with reference to FIG. 2. FIG. 2 is a block diagram illustrating an example of the radiation imaging apparatus. The radiation imaging apparatus includes a sensor array 201, a driving circuit 202, a reading circuit 220, and a driving control unit 230. The reading circuit 220 has a function for reading out a signal from a pixel. The driving control unit 230 can control the driving circuit 202 and the reading circuit 220.

Pixels are arranged on the sensor array 201 in a matrix state. For example, the pixel may be configured of a combination of a photoelectric conversion element 303 of a metal-insulator semiconductor (MIS) type or a positive-intrinsic-negative (PIN) type and a switching element (e.g., thin film transistor (TFT)) 302. Herein, the TFT may be preferably used as the switching element 302. The switching element 302 of each pixel is sequentially selected at each row by the driving circuit 202 via a gate line 301, so that an electric charge is output to a signal line 304. Then, the electric charge of each pixel is held by a sampling/holding circuit 203 via the signal line 304. Thereafter, the electric charge held by the sampling/holding circuit 203 is sequentially read out via a multiplexer 204. Then, a signal based on the read electric charge is amplified by an amplification circuit 210 and converted into a digital value by an A/D conversion unit 211. Every time the scanning of one row is completed, the driving circuit 202 sequentially drives a subsequent row on the sensor array 201 to execute scanning. By sequentially executing the above-described operations, the electric charges output from all of the pixels on the sensor array 201 may be converted into digital values. Thereafter, the driving control unit 230 controls the driving circuit 202 to execute a refresh operation of the sensor array 201 at an appropriate timing. The above operation is an example of an operation in which the driving circuit 202 executes scanning while the reading circuit 220 fixes the voltage applied to each of the signal lines 304, through which dark electric charges are discharged to execute initialization. The above-described driving and reading operations of the sensor array 201 are controlled according to the control of the driving control unit 230. Then, offset correction is executed on the image data converted into the digital value in which offset image data acquired from only a dark electric charge component without emitting the radiation is subtracted from radiation image data, and thus it is possible to acquire a captured image from which the unnecessary dark electric charge component is eliminated. Further, the driving control unit 230 can notify the other radiation imaging apparatuses of a predetermined state. In other words, in a case where one radiation imaging apparatus from among the plurality of radiation imaging apparatuses D1, D2, and D3 is notified of a predetermined state from another radiation imaging apparatus while the state of the one radiation imaging apparatus is different from the predetermined state, the driving control unit 230 can control the one radiation imaging apparatus to be the same state as the predetermined state. The predetermined state refers to a state of the radiation imaging apparatus determined based on the priority described below.

Next, a relationship between a radiation imaging apparatus and priority will be described with reference to FIG. 3. FIG. 3 is a table illustrating a relationship between a radiation imaging apparatus and priority. In FIG. 3, states of the radiation imaging apparatus and priority thereof are defined. The imaging control unit 112 (setting unit) sets the priority to the states of the radiation imaging apparatus. The imaging control unit 112 can set the priority with respect to each of the states in terms of re-imaging possibility, power-saving performance (based on power consumption), and durability. In other words, the priority is set based on a degree of possibility of being in a state where imaging is executable. Herein, example, the priority 1 is set to have the highest priority, while the priority with greater numerical value is set to have the lower priority. In other words, the priority that can be set by the imaging control unit 112 is set to a power-off state, an error state, a stand-by state, an imaging state, an imaging preparation completion state, and an imaging executable state in that order from the highest priority. An item to which the priority is set and a priority order thereof are not limited to the above, and thus the item or the priority order may be changed or replaced by the operation unit 114. Further, the above setting may be executed before radiation imaging, or may be changed while radiation imaging is being executed.

Figure 4:
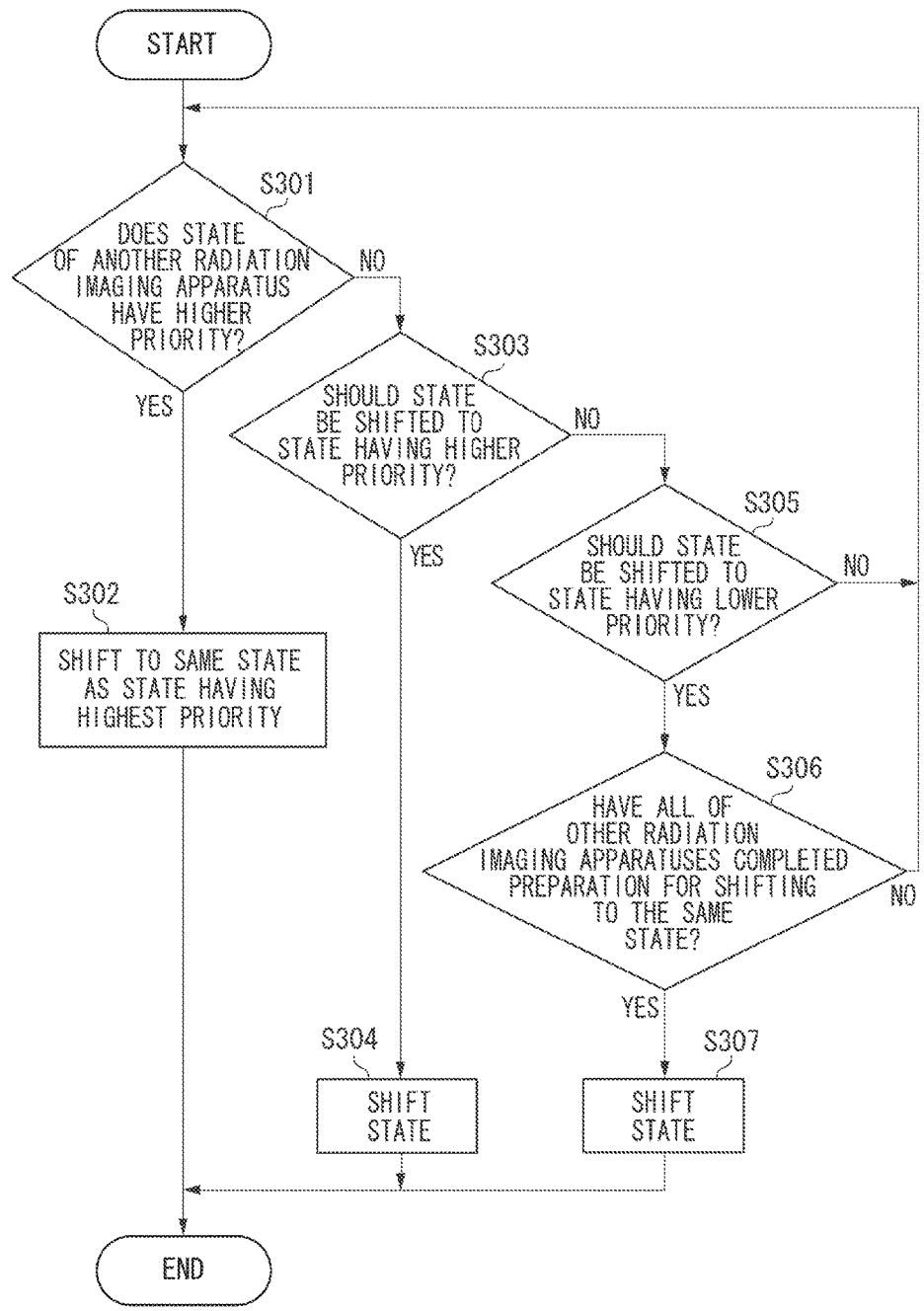
FIG. 4 is a flowchart illustrating an operation flow of each radiation imaging apparatus according to the first exemplary embodiment.

Next, transition of states of the radiation imaging apparatus according to the present exemplary embodiment will be described with reference to FIG. 4. FIG. 4 is a flowchart illustrating transitions of a state of one radiation imaging apparatus from among the radiation imaging apparatuses D1, D2, and D3. Hereinafter, respective steps of processing executed by the state control unit 1122 will be described based on the flowchart. The state of each radiation imaging apparatus is acquired by the acquisition unit 1121 and controlled by the state control unit 1122. Further, the priority is set by the setting unit (i.e., imaging control unit 112). Although only the radiation imaging apparatus D1 will be described below, the same control processing is applicable to the other radiation imaging apparatuses.

In step S301, the state control unit 1122 compares a state of the radiation imaging apparatus D1 with the states of the other radiation imaging apparatuses D2 and D3, and determines whether the priority order of the state of the radiation imaging apparatus D2 or D3 is higher than that of the radiation imaging apparatus D1. In a case where the priority order of the state of the radiation imaging apparatus D2 or D3 is higher than that of the radiation imaging apparatus D1 in step S301), the processing proceeds to step S302. In step S302, the state control unit 1122 shifts the state of the radiation imaging apparatus D1 to the same state as the state having the highest priority order from among the states of the radiation imaging apparatuses D2 and D3. In a case where the priority order of the states of the radiation imaging apparatuses D2 and D3 are not higher than that of the radiation imaging apparatus D1 (NO in step S301), the processing proceeds to step S303.

In step S303, it is determined whether the radiation imaging apparatus D1 should shift to a state having the priority higher than that of the current state. For example, the state where the shift is needed correspond to a case where an error has occurred when the radiation imaging apparatus D1 is in the stand-by state. In such a case, the radiation imaging apparatus D1 should shift to the error state the priority of which is higher than that of the current state. In a case where the radiation imaging apparatus D1 should shift to a state having the higher priority (YES in step S303), the processing proceeds to step S304. In step S304, the state of the radiation imaging apparatus D1 shifts. In a case where the radiation imaging apparatus D1 needs not shift thereto (NO in step S303), the processing proceeds to step S305.

In step S305, it is determined whether the radiation imaging apparatus D1 should shift to a state having the priority lower than that of the current state. For example, the state where the shift is needed corresponds to a case where the radiation imaging apparatus D1 has received an instruction for shifting to the imaging executable state from the imaging preparation completion state. In a case where the shift is needed (YES in step S305), the processing proceeds to step S306. In step S306, it is determined whether the other radiation imaging apparatuses D2 and D3 have completed the preparation for shifting to the same state. For example, in a case where the radiation imaging apparatus D1 receives an instruction for shifting to the imaging executable state from the imaging preparation completion state, the states of the radiation imaging apparatuses D2 and D3 are checked in order to determine whether the states thereof are shiftable to the imaging executable state. In a case where the states of the radiation imaging apparatuses D2 and D3 are shiftable (YES in step S306), the processing proceeds to step S307. In step S307, the radiation imaging apparatus D1 shifts to the imaging executable state. The acquisition unit 1121 and the state control unit 1122 similarly execute the above processing with respect to the radiation imaging apparatuses D2 and D3.

Figure 5:
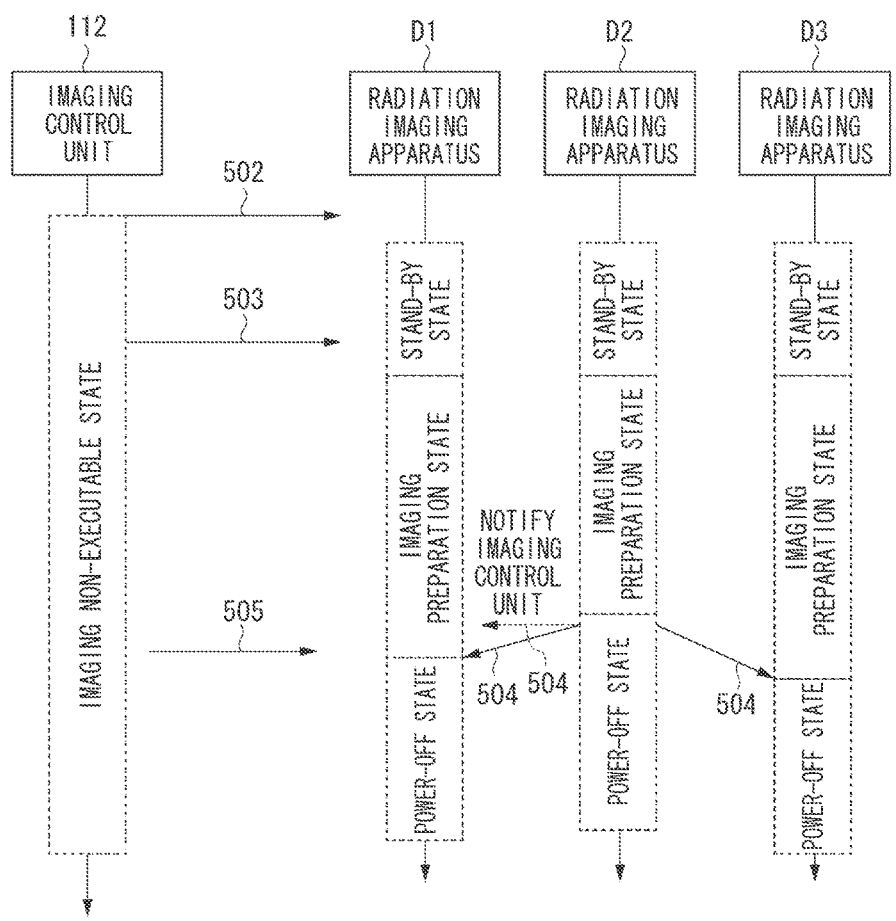
FIG. 5 is a state transition diagram illustrating transitions of a state of the radiography system according to the first exemplary embodiment.

Next, an operation of each unit to be executed when one of the plurality of radiation imaging apparatuses D1 to D1 according to the present exemplary embodiment has shifted to the power-off state from an imaging preparation state, will be described. FIG. 5 is a diagram illustrating states of the imaging control unit 112 and the radiation imaging apparatuses D1 to D3. In FIG. 5, "imaging non-executable state" refers to a state where the radiation imaging system S is in a state where imaging is not executable.

First, the operator registers the radiation imaging apparatuses to be used for the radiography system 107 through an operation input to the operation unit 114. Herein, the operator registers the radiation imaging apparatuses D1, D2, and D3.

Based on the operation input via the operation unit 114, the imaging control unit 112 transmits information 502 indicating that the radiation imaging apparatuses D1, D2, and D3 are used for the radiography system 107 to each of the radiation imaging apparatuses D1, D2, and D3. By receiving the information 502, the radiation imaging apparatuses D1, D2, and D3 recognize that the radiation imaging apparatuses D1, D2, and D3 are used for the radiography system 107. Then, upon recognition, each or the radiation imaging apparatuses D1, D2, and D3 shifts to a mode in which the state thereof is transferrable.

Next, in order to bring each of the radiation imaging apparatuses D1, D2, and D3 into the imaging preparation state from the stand-by state, the imaging control unit 112 transmits an instruction 503 for shifting the state to each of the radiation imaging apparatuses D1, D2, and D3. By receiving the instruction 503, each of the radiation imaging apparatuses D1, D2, and D3 shifts to the imaging preparation state. Herein, transitions of the states of the radiation imaging apparatuses D1, D2, and D3 will be described based on the correspondence relationship between the flowchart in FIG. 4 and the state transition diagram in FIG. 5. Since the states of other radiation imaging apparatuses are the stand-by state that is the same state as own state or each of the radiation imaging apparatuses D1, D2, and D3, a result of the determination in step S301 is "NO", so that the processing proceeds to step S303. Next, in step S303, since each of the radiation imaging apparatuses D1, D2, and D3 receives the instruction for shifting from the stand-by state to the imaging preparation state having the lower priority, a result of the determination in step S303 is "NO ", so that the processing proceeds to step S305. Next, since a result of the determination in step S305 is "YES", the processing proceeds to step S306. In step S306, since all other radiation imaging apparatuses are in the stand-by state and the stand-by state is a state shiftable to the imaging preparation state, a result of the determination in step S306 is "YES", and thus each of the radiation imaging apparatuses D1, D2, and D3 shifts to the imaging preparation state in step S307. All other radiation imaging apparatuses also shift to the imaging preparation state through the same processing flow.

Next, an operation to be executed when the radiation imaging apparatus D2 shifts to the power-off state from the imaging preparation state, will be described with reference to FIG. 5. For example, the above transition may occur when a power switch of the radiation imaging apparatus D2 is pressed. Alternatively, in a case where the radiation imaging apparatus includes a built-in battery, the above transition may occur when the battery is down or the power supplied thereto from the outside is stopped for some reason. As illustrated in the table in FIG. 3, the imaging control unit 112 (i.e., setting unit) sets the priority order of the power-off state to be higher than that of the imaging preparation state. Therefore, based on the priority order, the radiation imaging apparatus D2 shifts to the power-off state from the imaging preparation state. When the radiation imaging apparatus D2 shifts to the power-off state, information 504 indicating that the state thereof has been shifted is notified to the imaging control unit 112 and the radiation imaging apparatuses D1 and D3. By receiving the state notification command of the information 504, the radiation imaging apparatuses D1 and D3 recognize that the radiation imaging apparatus D2 has shifted to the power-off state. Then, used on the notified information 504, the radiation imaging apparatuses D1 and D3 shift to the same state as that of the radiation imaging apparatus D2. In addition, the notification method is not limited to the above method, and instead of directly notifying the radiation imaging apparatuses D1 and D3 of the information 504, the radiation imaging apparatus D2 may notify the state control unit 1122 of the information 504, so that the information 504 is notified by the state control unit 1122 based on the above notification. Then, the state control unit 1122 transmits a notification 505 to make the radiation imaging apparatuses D1 and D3 shift to the power-off state, which is the same state as that of the radiation imaging apparatus D2.

Through the above control, even in a case where one of the plurality of radiation imaging apparatuses D1 to D3 is shifted to the power-off state, the radiography system 107 can shift the states of the radiation imaging apparatuses D1 to D3 to the same state. In other words, in a case where at least one radiation imaging apparatus is not in the imaging executable state, the state control unit 1122 shifts all of the radiation imaging apparatuses D1 to D3 to the imaging non-executable state based on the information of the plurality of radiation imaging apparatuses D1 to D3 acquired by the acquisition unit 1121. Therefore, in a case where a long-length imaging is not executable by the radiography system 107 (i.e., not all of the radiation imaging apparatuses D1 to D3 are in the imaging executable state), it s possible to suppress the unnecessary power consumption. Further, through the above-described control, in a case where one radiation imaging apparatus is in a state where power consumption thereof is higher than that of other radiation imaging apparatuses (i.e., imaging executable state), the state is shifted to cause the power consumption to be lower based on the information of the plurality of radiation imaging apparatuses D1 to D3 acquired by the acquisition unit 1121. Therefore, it is possible to improve the usability of the radiography system 107 that executes long-length imaging.

Figure 6:
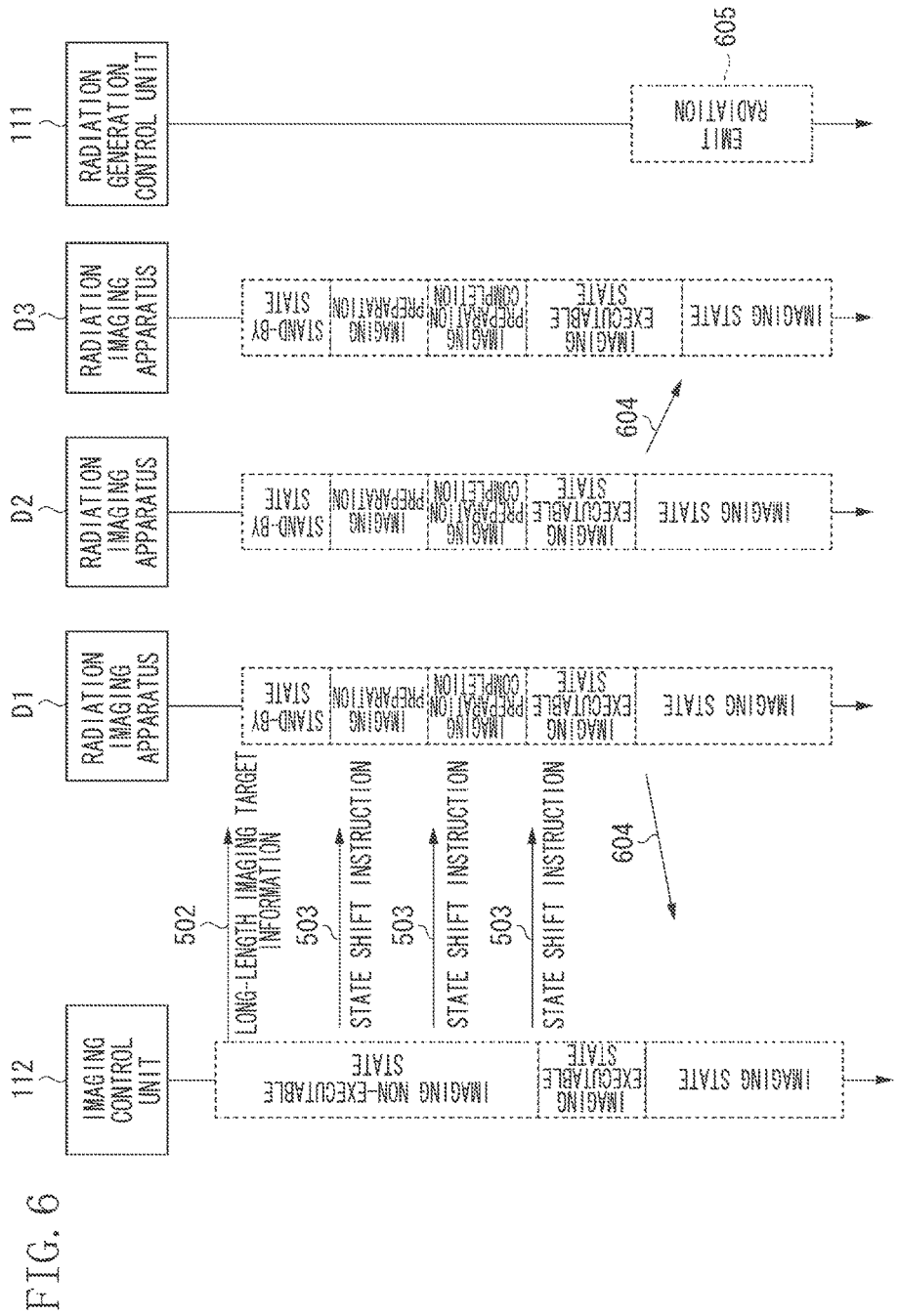
FIG. 6 is a state transition diagram illustrating transitions of a state of a radiography system according to a second exemplary embodiment.

A second exemplary embodiment will be described with reference to FIG. 6. In the present exemplary embodiment, an operation executed in an asynchronous imaging mode will be described. In the asynchronous imaging mode, as described above, the radiation imaging apparatuses D1, D2, and D3 do not adjust the imaging timing in synchronization with emission of radiation, but respectively start imaging by detecting the radiation incident thereto. With reference to FIG. 6, an operation of the radiography system 107, which is to be executed when a part of the radiation imaging apparatuses D1, D2, and D3 cannot detect the radiation incident thereto, will be described.

In the asynchronous imaging mode, the radiation imaging apparatuses D1, D2, and D3 execute imaging processing upon detecting the radiation emitted from the radiation source 108 Although each of the radiation imaging apparatuses D1, D2, and D3 detects the emission of radiation through individual processing, an amount of radiation that reaches each of the radiation imaging apparatuses D1, D2, and D3 may vary depending on a position of the subject. Therefore, there may be a case where a part of the radiation imaging apparatuses D1, D2, and D3 cannot determine whether the radiation is emitted, or determination thereof may be delayed. The following operation will be executed in order to suppress the above situation.

First, the imaging control unit 112 transmits information 502 indicating that the radiation imaging apparatuses D1, D2, and D3 are used for the radiography system 107 to the radiation imaging apparatuses D1, D2, and D3. By receiving the information 502, the radiation imaging apparatuses D1, D2, and D3 recognize that the radiation imaging apparatuses D1, D2, and D3 are used for the radiography system 107. Then, based on the recognition, each of the radiation imaging apparatuses D1, D2, and D3 shifts to a mode in which the state thereof is shiftable. Next, the imaging control unit 112 transmits a state transition instruction 503 to the radiation imaging apparatuses D1, D2, and D3. Based on the instruction 503, each of the radiation imaging apparatuses D1, D2, and D3 can sequentially shift to the imaging preparation state, the imaging preparation completion state, and the imaging executable state from the stand-by state in that order.

Next, in a state where the radiation imaging apparatuses D1, D2, and D3 have shifted to the imaging executable state, the radiation generation control unit 111 causes the radiation source 108 to emit radiation. The radiation imaging apparatuses D1 and D2 detect the emission of radiation and shift to the imaging state. In this case, the radiation imaging apparatuses D1 and D2 can shift to the imaging state having a priority which is higher than that of the imaging executable state. Herein, although the radiation imaging apparatuses D1 and D2 have shifted to the imaging state, the radiation imaging apparatus D3 has not detected the emission of radiation. At that time, the radiation imaging apparatuses D1 and D2 are in the imaging state, and thus the priorities thereof are higher than that of the radiation imaging apparatus D3 that is in the imaging executable state. Therefore, the radiation imaging apparatus D3 shifts to the imaging state, which is the same state as the states of the other radiation imaging apparatuses D1 and D2. More specifically, the radiation imaging apparatus D1 or D2 that has detected the emission of radiation notifies the imaging control unit 112 of a state 604. Based on the above notification, the imaging control unit 112 causes the radiation imaging apparatus D3 that has not yet shifted to the imaging state to shift to the imaging state. Alternatively, the radiation imaging apparatus D1 or D2 may directly notify the radiation imaging apparatus D3 of the state 604. The driving control unit 230 of the radiation imaging apparatus D3 can shift the state to the same state based on the notified state 604.

Through the above control, even in a case where one of the plurality of radiation imaging apparatuses D1, D2, and D3 cannot execute imaging, the radiography system 107 can shift to the state where the imaging is executable. Therefore, it is possible to suppress the state in which a part or the radiation imaging apparatuses D1, D2, and D3 cannot execute imaging. Therefore, the radiography system 107 according to the present exemplary embodiment can suppress the possibility of executing imaging again because of failure in long-length imaging.

Figure 7:
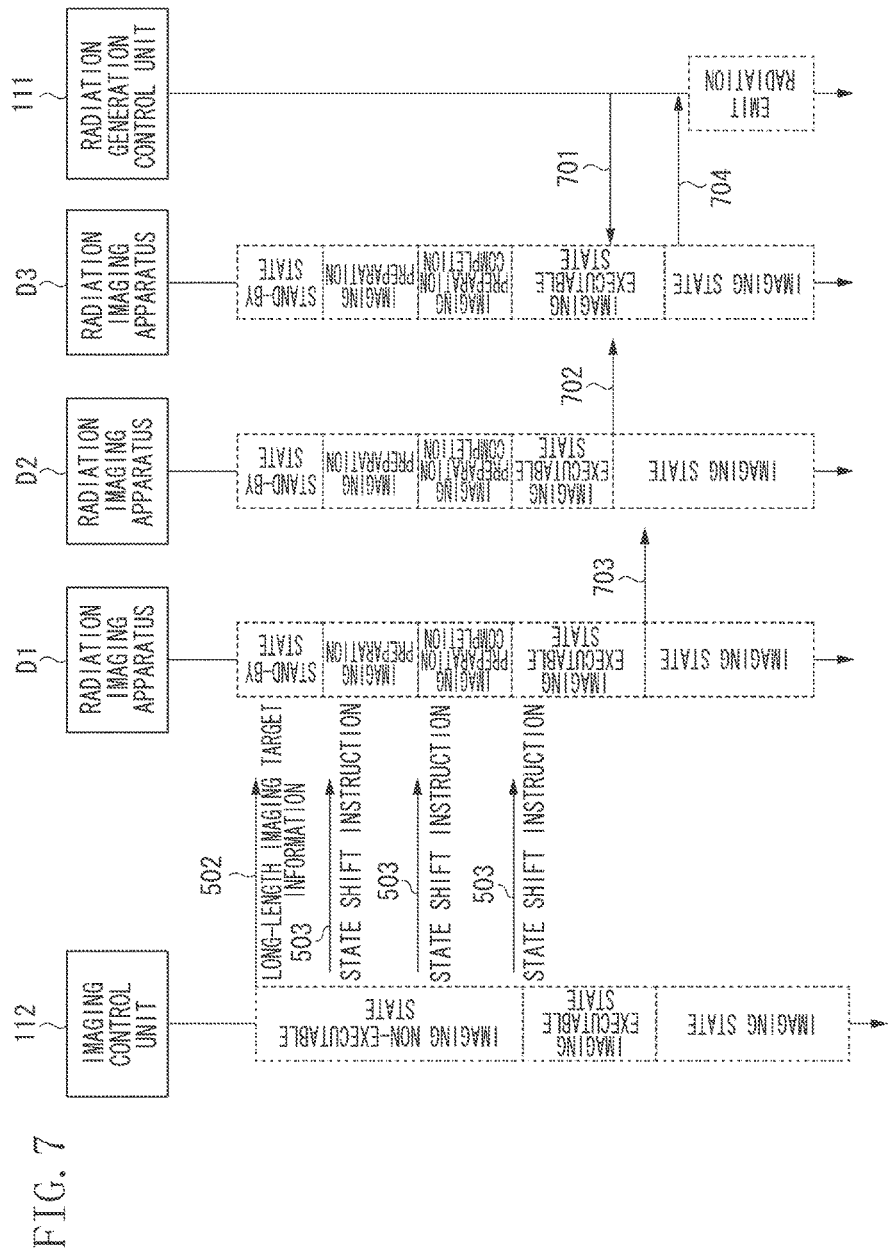
FIG. 7 is a state transition diagram illustrating transitions of a state of a radiography system according to a third exemplary embodiment.

A third exemplary embodiment will be described with reference to FIG. 7. In the present exemplary embodiment, an operation executed in a synchronous imaging mode will be described. In the synchronous imaging mode, as described above, a synchronization signal is transmitted/received between each of the radiation imaging apparatuses D1, D2, D3 and the radiation source 108, so that the imaging timing is adjusted to synchronize the timing of the emission of radiation. The transmission and reception of the synchronization signal can be realized through a wired or a wireless communication means. In the present exemplary embodiment, for example, each of the radiation imaging apparatuses D1, D2, and D3 communicates with the radiation source 108 and previously adjusts a timing between imaging and X-ray emission. The operation thereof will be described in detail below.

Similar to the above-described exemplary embodiments, at first, the imaging control unit 112 brings the radiation imaging apparatuses D1, D2, and D3 into the imaging executable state. Then, the imaging control unit 112 transmits a command 701 for requesting the radiation source 108 to emit radiation to the radiation imaging apparatuses D1, D2, and D3. For example, the command 701 may be transmitted to the radiation imaging apparatuses D1, D2, and D3 when a radiation emission switch connected to the radiation source 108 is pressed by the operator.

In a case where each of the radiation imaging apparatuses D1, D2, and D3 shifts to the imaging state, a timing of state transition will not be adjusted with that of the other radiation imaging apparatuses. When the state thereof is shifted to the imaging state, a radiation emission permission command 702, 703, or 704 is transmitted to the radiation generation control unit 111. The radiation generation control unit 111 does not respond to the command 702, 703 or 704 received from each of the radiation imaging apparatus D1, D2, or D3, and emits radiation when the commands 702, 703, and 704 have been received from all of the radiation imaging apparatuses D1, D2, and D3. Through the above-described control, even in a case where there is a difference in response time between the plurality of radiation imaging apparatuses D1, D2, and D3 in the synchronous imaging mode, degradation of image quality or imaging failure occurring in long-length imaging can be suppressed.

Through the above-described control, the radiography system for executing long-length imaging is capable of suppressing the possibility of re-imaging even in a case where the imaging is executed in a state of synchronizing a plurality of radiation imaging apparatuses with the radiation source.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-067070, filed Mar. 27, 2015, which is hereby incorporated by reference herein in its entirety.

What is claimed is:

1. A radiography system for executing long-length imaging using a plurality of radiation imaging apparatuses, the radiography system comprising:
a processor coupled to a storage medium storing a program that when executed causes the processor to function as,
an acquisition unit configured to acquire state information for each of the plurality of radiation imaging apparatuses; and
a state control unit configured to control a change of state of at least one of the plurality of radiation imaging apparatuses to a same state as that of another radiation imaging apparatus from among the plurality of radiation imaging apparatuses based on the state information acquired by the acquisition unit in the case that the at least one of the plurality of radiation imaging apparatuses is in a state where the power consumption is higher than that of the another radiation imaging apparatus having a different state,
wherein the state information includes information indicating whether or not each radiation imaging apparatus is in an imaging state, and
wherein the state control unit changes the state of each of the plurality of radiation imaging apparatuses into the imaging state based on the state information acquired by the acquisition unit in the case that at least one radiation imaging apparatus from among the plurality of radiation imaging apparatuses is in the imaging state.

2. The radiography system according to claim 1, wherein the state information includes information indicating whether or not a radiation imaging apparatus is turned on.

3. A radiography system for executing long-length imaging using a plurality of radiation imaging apparatuses, the radiography system comprising:
a processor coupled to a storage medium storing a program that when executed causes the processor to function as,
an acquisition unit configured to acquire state information for each of the plurality of radiation imaging apparatuses; and
a state control unit configured to control a change of state of at least one of the plurality of radiation imaging apparatus to a same state as that of another radiation imaging apparatus from among the plurality of radiation imaging apparatuses based on the state information acquired by the acquisition unit in the case that the at least one of the plurality of radiation imaging apparatuses is in a state where the power consumption is higher than that of the another radiation imaging apparatus having a different state;
wherein the state control unit changes a state of the at least one of the plurality of radiation imaging apparatuses to a state having a lower power consumption based on the state information acquired by the acquisition unit in the case that the at least one radiation imaging apparatus is in a state where the power consumption is higher than that of another radiation imaging apparatus having a different state.

4. The radiography system according to claim 3, further comprising a display unit configured to display a state of a part of radiation imaging apparatuses from among the plurality of radiation imaging apparatuses.

5. The radiography system according to claim 3, wherein each of the plurality of radiation imaging apparatuses includes a radiation detection panel configured to convert detected radiation into an image signal.

6. A radiography system for executing long-length imaging using a plurality of radiation imaging apparatuses, the radiography system comprising:
a processor coupled to a storage medium storing a program that when executed causes the processor to function as,
an acquisition unit configured to acquire state information for each of the plurality of radiation imaging apparatuses;
a state control unit configured to control a change of state of at least one of the plurality of radiation imaging apparatus to a same state as that of another radiation imaging apparatus from among the plurality of radiation imaging apparatuses based on the state information acquired by the acquisition unit in the case that the at least one of the plurality of radiation imaging apparatuses is in a state where the power consumption is higher than that of the another radiation imaging apparatus having a different state; and
a setting unit configured to set a state priority with respect to each of the states to the plurality of radiation imaging apparatuses,
wherein the state priority is set based on a degree of possibility of being in a state where imaging is executable.

7. The radiography system according to claim 6, wherein the setting unit sets the state priority as any one of a stand-by state, an imaging preparation state, and an imaging executable state in that order from highest priority to lowest priority.

8. The radiography system according to claim 6, wherein, in a case where one radiation imaging apparatus from among the plurality of radiation imaging apparatuses is in a state where the priority set by the setting unit is higher than that of another radiation imaging apparatus, the one radiation imaging apparatus is shifted to a same state as that of the another radiation imaging apparatus.

9. A control method of a control apparatus that controls long-length imaging using a plurality of radiation imaging apparatuses, the control method comprising:
   acquiring state information for each of the plurality of radiation imaging apparatuses;
   controlling a change of state of at least one of the plurality of radiation imaging apparatus to a same state as that of another radiation imaging apparatus from among the plurality of radiation imaging apparatuses based on the state information acquired by the acquisition unit in the case that the at least one of the plurality of radiation imaging apparatuses is in a state where the power consumption is higher than that of the another radiation imaging apparatus having a different state: and
   changing a consumption state of at least one of the plurality of radiation imaging apparatuses to a same state as that of another radiation imaging apparatus from among the plurality of radiation imaging apparatuses based on the acquired state information in the case that the power consumption state of the at least one of the plurality of radiation imaging apparatuses is higher than power consumption of the another radiation imaging apparatus.

10. A non-transitory computer-readable storage medium storing a program that when executed on a computer causes the computer to execute the control method according to claim 9.

* * * * *